United States Patent [19]

Dear et al.

[11] Patent Number: 5,139,628
[45] Date of Patent: Aug. 18, 1992

[54] PROCESS FOR THE PREPARATION OF 4-SULFO-2-CHLOROBENZOIC ACID

[75] Inventors: Kenneth M. Dear; Kevan M. Reeve; Philip J. Turner, all of Widnes, United Kingdom

[73] Assignee: Interox Chemicals Limited, London, England

[21] Appl. No.: 674,380

[22] PCT Filed: Sep. 12, 1989

[86] PCT No.: PCT/GB89/01068

§ 371 Date: Apr. 11, 1991

§ 102(e) Date: Apr. 11, 1991

[87] PCT Pub. No.: WO90/02731

PCT Pub. Date: Mar. 22, 1990

[30] Foreign Application Priority Data

Sep. 15, 1989 [GB] United Kingdom ............... 8821649

[51] Int. Cl.$^5$ ............................................. C07F 9/6547
[52] U.S. Cl. ................................. 204/157.79; 562/418
[58] Field of Search ................. 558/56; 562/418; 204/157.76, 157.77, 157.78, 157.79

[56] References Cited

U.S. PATENT DOCUMENTS 2,666,785  1/1954  Feichtinger et al. ............... 562/56
3,151,153  9/1964  Keith et al. ........................ 562/54

FOREIGN PATENT DOCUMENTS

WO90/2731  3/1990  PCT Int'l Appl. .
365060  12/1962  Switzerland .

OTHER PUBLICATIONS

Robert T. Morrison, Robert N. Boyd, Organic Chemistry, 3rd Edition, Allyn and Bacon, Inc., Boston, 1975, pp. 47-62.

Chemical Abstracts, vol. 80, No. 9, Mar. 1974, (Columbus, Ohio, US), see p. 332, abstract 47649k & CS, A, 15000 (J. Horyna, et al.), Aug. 15, 1973 & Chemical Abstracts, 9th Collective Index, 1978, p. 2064f, formula $C_7H_5ClO_5S$.

Primary Examiner—John Niebling
Assistant Examiner—Dean Nguyen
Attorney, Agent, or Firm—Larson and Taylor

[57] ABSTRACT

A multi stage process for the conversion of 2-chloro-4-sulphotoluene (SCT) to 2-chloro-4-sulphobenzoic acid (SCUBA). Stage (a) comprises a process S1 for the selective side chain bromination of SCT to 2-chloro-4-sulpho-dibromotoluene (SCDBT) or 2-chloro-4-sulpho-bromotoluene (SCMBT) by contacting the starting material with bromine in chloroform or trichloroethane and irradiating the mixture with light that dissociates bromine. Subsequently, in stage (b), process S2, the product of S1 can be hydrolysed at elevated temperature after separation from the organic solvent to the corresponding alcohol (SCOL) or aldehyde (SCAB). In stage (c), the product of S2 can be oxidized to SCUBA either by oxidation with a peroxyacid, optionally generated in situ, provided that the aqueous solution has previously been stripped of bromide/bromine in process S3. The oxidation can also be carried out using bromine, preferably generated in situ in process S5 by oxidation of residual bromide with hydrogen peroxide, which can then be followed by process S3 to strip out the bromine/bromide. A combination of processes S1, S2, S5 and S3 in that order provides a closed loop process cycle which recycles the environmentally harmful reagent, bromine.

31 Claims, No Drawings

PROCESS FOR THE PREPARATION OF 4-SULFO-2-CHLOROBENZOIC ACID

The present invention relates to the halogenation and oxidation of substituted alkyl benzene compounds and specifically to the halogenation and oxidation of the alkyl substituent in compounds that are further substituted by both a halo and a sulpho group.

One of the compounds that is of potential value as an intermediate in for example agrochemical preparations is 4-sulpho-2-chlorobenzoic acid, which is sometimes also referred to herein by the abbreviation "SCUBA". A suitable starting material for the preparation of this compound is the corresponding 2-chlorotoluenesulphonic acid which itself can be made conveniently by instant inventors team by nuclear chlorination of toluenesulphonic acid. Whilst in theory direct oxidation of the methyl substituent of the compound is possible, using for example potassium permanganate, such a reagent is normally difficult to regenerate, produces insoluble manganese dioxide powder as a by-product and is accordingly regarded unfavourably for bulk-scale activities.

It would be desirable to find an alternative route for the preparation of 4-sulpho-2-chlorobenzoic acid which employed a regenerable reagent and/or avoided the difficulties associated with production of a fine powder as byproduct.

The team investigating ways of providing such an alternative route has also been investigating oxidation of the methyl substituent in toluene to the carboxylic acid in a related molecule in which the benzene nucleus is substituted by a nitro substituent instead of by a sulpho substituent. The team investigated a multi-stage process in the first stage of which the methyl substituent was brominated, in the second stage of which the brominated substituent was hydrolysed to an alcohol or aldehyde and in the third stage of which, the second stage product was oxidised to the carboxylic acid. It was found by the team that when a nitro-substituent was present, the first stage could be carried out conveniently in a two phase aqueous/hydrophobic system employing hydrogen peroxide and hydrogen bromide to generate bromine in the aqueous phase which is maintained in contact with the organic substrate in the organic phase and irradiated with bromine-dissociating radiation. By carrying out such a process under appropriately selected processing conditions, they found that it was possible to obtain as product the dibrominated side-chain product to a reasonably high extent of selectivity. The resultant product could be hydrolysed reasonably well in a subsequent step to the corresponding aromatic aldehyde, whereas if the product of the bromination step comprised either mainly or a substantial fraction of the corresponding monobrominated side chain product, the subsequent hydrolysis step was found to be markedly more difficult with much reduced yield.

There is a substantial degree of similarity between nitrotoluene and 2-chloro-4-toluene sulphonic acid, in that for example both molecules contain a methyl substituent that is available for bromination and both contain a deactivating substituent. Accordingly, it might be anticipated reasonably that a similar technique might be employed successfully in respect of 2-chloro-4-toluene sulphonic acid as starting material and that similar constraints would apply in respect of the bromination and hydrolysis steps. However, it was found in an initial appraisal of the process that adoption of the bromination technique without substantial modification resulted in a surprisingly poor yield of side chain brominated product. Secondly, it was found that the constraints upon subsequent processing steps, including that of hydrolysis were markedly different from expectations. Thus, the inventors have found that certain changes were necessary and other changes unexpectedly became possible.

The inventors have identified a convenient multi-stage route for the preparation of 4-sulpho-2-chlorobenzoic acid (SCUBA) from 2-chloro-4-toluene sulphonic acid (SCT) in which in stage a, the methyl substituent in the alkylbenzene is selectively brominated, in stage b, the product of stage a is hydrolysed to the corresponding alcohol or aldehyde and in stage c, the product of stage b is oxidised to the corresponding carboxylic acid.

According to one aspect of the present invention there is provided a multi-stage process for the preparation of SCUBA from SCT characterised in that in stage a, the methyl substituent in SCT is selectively brominated to the mono and/or dibrominated compound by reacting the SCT in a substantially anhydrous solvent with bromine that has been dissociated into radicals by radiation, in stage b, the selectively brominated compounds produced in stage a are extracted into an aqueous phase and hydrolysed to the corresponding alcohol or aldehyde in the presence of hydrogen bromide and in stage c, the aqueous solution of aldehyde/alcohol produced in stage b is oxidised to SCUBA by reaction with a percarboxylic acid in the substantial absence of hydrogen bromide or by reaction with bromine.

According to one particular aspect of the invention, there is provided a a process (S1) for the side chain bromination of an alkyl substituent of a further substituted benzene compound which can be incorporated as stage a in a multi-stage process for the preparation of a substituted benzoic acid (SCUBA) from a correspondingly substituted alkylbenzene (SCT), characterised in that the alkylbenzene compound employed is 2-chloro-4-toluene sulphonic acid (SCT), which is dissolved in an anhydrous or substantially anhydrous solvent selected from chloroform and trichloroethane and is contacted with an effective amount of bromine per mole of 2-chloro-4-toluene sulphonic acid at a temperature of from 30° C. to the boiling point of the reaction mixture and the reaction mixture is irradiated with bromine-dissociating radiation until at least some 1-dibromomethyl-2-chloro-4-sulphobenzene (SCDBT) has formed.

The detection of SCDBT in the reaction mixture in practice confirms that a substantial proportion of the substrate has been brominated in the methyl substituent to either the aforementioned SCDBT or the corresponding monobrominated compound, SCMBT, 1-bromomethyl-2-chloro-4-sulphobenzene.

It will be recognised that although the S1 process could be employed by itself as a means to produce a side-chain brominated product or products for use in other processes, it is particularly suitable as the first stage of a bi or multi stage process resulting in the formation of respectively the corresponding alcohol/aldehyde or carboxylic acid from SCT.

In process S1, it would be possible at least in theory to substitute for the solvent, chloroform or 1,1,2-trichloroethane, a number of other hydrocarbon or halogenated hydrocarbon solvents that have a boiling point in excess of about 40° C., but the present investigations show that it would be significantly less efficient to employ such substitute solvents for this particular reaction. Thus, use of such commonly employed solvents as cyclohexane, dibromoethane, and tetrachloroethane result in either very little reaction to form the desired SCDBT from SCT or a very much retarded rate of reaction under otherwise similar reaction conditions. A further widely used solvent, 1,1,2,2-tetrachloro-ethene, was also unusable because it reacted itself too rapidly with the bromine. Moreover, although both of the selected solvents could be readily employed when the the other process conditions were arranged so as to produce primarily SCMBT, it was found by the inventors that it became decreasingly practical to employ 1,1,2-trichloroethane as the process conditions were changed towards producing an increasing proportion of SCDBT. Such a sensitivity of the reaction system to the choice of solvent is somewhat surprising and indicates that those criteria applicable to the reaction of related starting materials, even using a bromine or bromine-generating reactant, cannot be transposed indiscriminately to the instant starting material, SCT.

It is particularly desirable to employ a substantial excess of solvent beyond that needed to attain complete dissolution of the starting material. By so doing, it is possible to accelerate the reaction towards the specific preparation of SCMBT and SCDBT rather than to any other brominated product such as ring brominated compounds and away from loss of bromine reactant from the reaction mixture. By so choosing the preferred dilute solution, it is believed the the penetration of the bromine-dissociating radiation into the reaction mixture is improved, which not only has the effect of improving the efficiency of production of SCMBT/SCDBT, but also assists the efficiency of utilisation of the radiation.

It is preferable to employ a concentration of SCT of up to about 2M, i.e. up to about 500 g/l, and particularly in the range of 0.25 to 1.25M. To some extent, the more preferred extent of dilution depends upon the extent to which it is desired to produce SCDBT relative to SCMBT. For a product that is primarily SCMBT, the range of 0.5 to 1.25M is more preferable, whereas for producing a product that is primarily SCDBT, the range of 0.25 to 1.0 is more preferable. Lower concentrations than 0.25M are feasible technically, such as 0.05 to 0.25M, or even lower, and accordingly could be employed if the user wanted to use them, but suffer from a lower space yield than in the particularly preferred region and thus such concentrations increase the capital cost for the process.

A matter of some importance in the operation of the S1 process comprises the water content of the reaction mixture that can be tolerated for the instant reaction. Unlike in the case of side-chain bromination of nitro-substituted alkyl-benzenes, the S1 process responds unfavourably to the presence of water. Comparative experimentation showed that water caused both the extent of conversion of SCT and the yield of the desired product SCDBT to decrease significantly, so that the difficulty is not simply a further reaction of the product of bromination, but is associated with the initial reaction itself. This was an unexpected constraint upon the research team seeking to carry out a controlled oxidation of SCT ultimately to SCUBA, and particularly upon the first step in the overall process.

Without wishing to be bound to any particular theory, the inventors postulated that the sidechain bromination reaction is carried out in two stages, the first stage resulting in the formation of monobromo substituted methyl substituent (SCMBT), which in the second stage further brominated to form SCDBT. The first stage is now believed to progress more quickly than the second, so that the content of SCMBT in the reaction mixture increases quickly at the start of the reaction and then more slowly is converted to SCDBT. However, when a substantial volume of water is also present, an aqueous phase is formed that takes up hydrogen bromide as it is generated as a by-product from the bromine and this solution is capable of hydrolysing SCMBT under the mild temperature conditions prevailing at a rate that is of a similar order of magnitude to the desired second stage. This by itself might have been considered not to be too serious a problem in the context of an overall process to produce SCUBA from SCT, but it is further believed that the alcohol formed can itself react with more SCMBT to form an ether, although the actual impurity compound formed in a substantial amount has not yet been identified. In consequence, a substantial part of the SCT starting material is diverted to impurities in a way that did not happen when the related starting materials were tested previously.

Irrespective of whether the above explanation is correct, the practical consequence is that the use of hydrogen peroxide to generate or regenerate bromine in situ cannot be contemplated. Accordingly, it is a condition imposed on the S1 reaction process that the solvent for the reaction is either anhydrous or contains less than the amount of water which interferes significantly with the reaction to selectively form SCDBT. This constraint becomes of increased relevance in the context of a multi or di-stage process and/or if hydrogen peroxide is used to regenerate bromine in a subsequent or an external functional stage, and especially when solvent recycle is employed. It is accordingly preferred to effect suitable water/solvent separation before solvent recycle such that the there is no separate aqueous phase present in the reaction mixture during the S1 process.

A further factor of some importance to the overall efficiency of the process is the mole ratio of bromine to SCT employed in the reaction mixture. The stoichiometric requirement for the desired product is 1 or 2 moles of bromine per mole of SCT, to produce respectively the mono and dibrominated substrate, but in practice it has been found that a significant excess of bromine is required. Thus, to obtain a substantial conversion of the substrate, viz at least 90% and in many instances at least 95%, the mole ratio of bromine:SCT is normally at least 1:6:1. At mole ratios in the region of about 1.8:1 to 2.2:1, the major product is SCMBT.

Broadly speaking, as the mole ratio is increased, the proportion of SCDBT also tends to increase, always assuming that the reaction is permitted to continue until the bromine has been consumed. If it is desired that SCDBT is the major product, the mole ratio is conveniently selected within the range of 2.8:1 to 4:1 and in many instances will be selected in the range of about 2.9:1 to 3.2:1. The latter range, in particular, for selective SCDBT production, represents a balance between the beneficial influence of excess reagent on directing the product mix towards the desired dibrominated product and the potentially disadvantageous effect of impairing light penetration as the bromine concentration increases.

The reaction is conveniently carried out at a temperature at or approaching the reflux temperature of the reaction mixture, i.e. normally in the range of about 50° to about 70° C. when the solvent is chloroform and preferably from about 70° to 85° C. when the solvent is 1,1,2-trichloroethane.

The radiation illuminating the reaction has as its object the dissociation of bromine into bromine radicals. Thus, the effective radiation has a wavelength of not more than 600 nm. A significant proportion of useful radiation is available from lamps which have principal emissions in the range of 600 to 250nm. Lamps which are described as daylight lamps have been found particularly suitable for the instant invention since the greater part of their radiation is emitted within the preferred wavelength range. Suitable lamps are often described as high pressure sodium discharge lamps (SON), mercury fluorescent lamps (MBF) and tungsten or tungsten halogen lamps. It will be recognised that there is a relationship between effective radiation intensity and reaction rate and consequently also with reaction period, the more intense the radiation, the faster the rate and shorter the reaction period needed to achieve the desired generation and utilisation of the bromine reactant.

It will also be understood that the actual design of the apparatus employed will contribute significantly to effectiveness of employment of the radiation, including external factors such as the ratio of reaction volume to illuminated surface area. Radiation lamps can for example be positioned above the surface of the reaction mixture and/or immersed within it. Alternatively or additionally the vessel wall can be provided with translucent ports through which the radiation is shone into the reaction mixture. Reflectors can be used to minimise radiation losses. By way of guidance only, on a laboratory scale, we have found that a daylight spectrum lamp having a nominal luminous flux of 8500 to 9500 lumens set at a distance of about 10 to 25cms from the reaction vessel, permits the reaction to progress to completion within a reasonable period, normally from about 2 to about 4 hours after the bromine has been introduced.

It is of practical importance to take into account internal factors that affect the efficiency of utilisation of the radiation employed, when designing more suitable reaction vessels for this reaction. These factors include the ratio of reaction volume to illuminated surface area and the maximum effective path length of the radiation in the reaction mixture, which will itself correlate with the concentrations of light absorbers in the mixture. The interaction between the two factors determines the proportion of reaction volume that is effectively illuminated at any time. As the proportion falls away from 100% of the volume, the reaction time tends to lengthen. The actual design of the reaction vessel is within the control of the process operator and in preference the apparatus will be selected or modified so as to minimise or eliminate volumes of reaction mixture that are not penetrated by the radiation directly, or will employ preferably efficient mixing of the reaction mixture so as to increase the likelihood of all the reaction mixture containing bromine and substrate passing frequently through an illuminated zone of the reaction vessel.

The bromine could theoretically all be present at the start of the reaction period, but this would inevitably maximise bromine concentration and hence retard the reaction rate by impairing light penetration during the early part of the reaction period. Self-evidently, the importance of this as a constraint depends to at least some extent on the nature of the apparatus employed, it being more important as the path length of light in the reaction mixture increases. A preferable method comprises the progressive introduction of all or the major proportion of the bromine into the reaction mixture during a substantial proportion of the reaction period, or possibly during more than one part of the reaction period.

In a convenient and advantageous process the reaction mixture contains initially from substantially none up to about 1 mole of bromine per mole of SCT and the remainder of the bromine is introduced gradually, which will accordingly be from about 1 to 3 moles of bromine per mole SCT, depending upon total mole ratio selected and the mole ratio present initially. It is often convenient for the or each bromine introduction period to last about 2 to 6 hours and a subsequent reaction period to last from 3 to 5 hours, giving a combined introduction plus subsequent reaction period of about 5 to 9 hours. Selection of the overall reaction period depends on the apparatus employed, as indicated herein before, the manner of introduction of the bromine, the mole ratio of bromine to substrate and instantaneous concentration of the bromine. It can be varied over a very wide range of periods from about 2 hours to over 10 hours, such as up to 15 hours. It is often convenient to express the period of bromine introduction as preferably at least 40% of the overall reaction period and especially from about 50% to about 85% of the overall reaction period.

It has been observed that conversion of SCT to SCMBT and further bromination of SCMBT to SCDBT continues slowly after all the bromine has been introduced. Thus, it is often a desirable practice to analyse samples of the reaction mixture at intervals thereafter for SCT, SCMBT and SCDBT, for example by conventional HPLC techniques to determine the ratio of the species and to employ the findings as a basis for deciding when to terminate the reaction. It is a commercial judgement to balance the cost of allowing the reactions to continue (decreased throughput, increased processing costs) against the benefit of increased conversion and utilisation of bromine.

A convenient time to stop depends in practice upon the future intended use of the product. If SCDBT is desired as the major product, the practical time to stop is often at the point in time after all the SCT has been consumed when the molar ratio of SCMBT to SCDBT reaches a ratio selected between 1:8 to 1:99. In one particularly preferred set of conditions, it is possible to obtain conversion from SCT to SCDBT of at least 90 to 95% and of residual SCMBT of around 5% to 2%, based on the moles of SCT employed. If on the other hand, the user can be tolerant of high or major SCMBT content, as is now found to be the case if he wishes to make SCUBA, he will tend to stop when there is still a fairly minimal, such as 5% or less SCT remaining.

The reaction of process S1 is especially well suited to a batch processing technique, but it will be recognised that it can be engineered to be operated continuously using a flow-through technique, the rate of flow of the reaction mixture through the illuminated reaction vessel being adjusted so as to provide the desired reaction period.

At the end of the reaction, the reaction products are all present dissolved in the reaction mixture, with the exception of the fraction of hydrogen bromide and bromine that was stripped out of the mixture in effluent gases. SCDBT can be recovered from solution simply by cooling the mixture, such as to ambient temperature or below, whereupon it precipitates. The precipitate can be purified by solvent washing, using a liquid hydrocarbon or halogenated hydrocarbon and/or by a conventional hot dissolution and cooling reprecipitation technique from such solvents.

The chloroform or trichloroethane mother liquor can be recycled for the preparation of further SCDBT or SCMBT, preferably after it has been analysed for residual SCMBT, SCT, if any, and bromine/bromide contents. The appropriate reagent additions can then be made to repeat process S1 in accordance with the foregoing disclosures, together with any extra solvent to compensate for losses into the effluent gases or with the precipitate.

Advantageously it is not necessary, however, to recover any SCDBT or SCMBT as a solid product from the reaction mixture before it can be processed further as part of a process for the eventual production of SCUBA. When it is desired to form 2-chloro-4-sulphobenzaldehyde (SCAB) from SCDBT and 2-chloro-4-sulphobenzyl alcohol (SCOL) from SCMBT, it can be carried out with or without separation of the SCDBT or SCMBT from its chloroform or trichloroethane solution.

In this, the second aspect of the instant invention, there is provided a process, S2, for the preparation of 2-chloro-4-sulpho-benzaldehyde (SCAB) from SCDBT or 2-chloro-4-sulphobenzyl alcohol (SCOL) from SCMBT, or any mixture thereof which process is characterised by the steps of:

i. abstracting SCDBT and SCMBT into aqueous solution by contacting the SCDBT and SCMBT in a non-aqueous phase with water,
ii. separating the aqueous solution of SCDBT and SCMBT from any residual non-aqueous phase that has a boiling point significantly below 85° C.,
iii. bringing the aqueous solution to a temperature of at least about 85° C. up to the boiling point of the solution, and
iv. maintaining the aqueous solution at that temperature until at least a proportion of the SCDBT and the SCMBT has been hydrolysed to SCAB and to SCOL respectively.

It will be understood that the non-aqueous phase of SCDBT and SCMBT in step i can comprise either solid material, such as a precipitate of SCDBT obtained from process S1 described hereinbefore, or more conveniently for commercial operation, the phase can alternatively comprise the chloroform trichloroethane solution containing SCDBT and SCMBT prepared in process S1. In the latter case, it will be understood that the chloroform solution will typically have a temperature of about 50° to 65° C. at the end of the S1 reaction period and the trichloroethane solution a corresponding temperature of about 80° to 85° C. The non-aqueous solution can be contacted with water at that temperature or allowed to cool, if desired before aqueous extraction. Sufficient water is employed, preferably, for substantially all the SCDBT and SCMBT to pass into solution, thereby avoiding substrate losses upon the separation of the two phases. Although it is in contact with water, under such conditions it has been found that ring hydrolysis of the SCDBT and SCMBT is minimal. It is possible to employ more water than is needed to form a saturated solution. By way solely of demonstration, it is convenient to employ up to about 1 liter of water per mole of SCDBT, and often at least 0.2 liters per mole of SCDBT. Higher volume ratio of water:SCDBT can be used if desired, but at a lower space yield.

When the non-aqueous phase comprises a solution of the SCDBT or SCMBT in the selected chlorinated hydrocarbon solvent, its separation from the aqueous phase is most suitably carried out in step ii. The two liquid phases can be separated by standard physical liquid-liquid separating devices, relying for example on their density difference.

The aqueous phase is heated to a temperature in excess of 85° C., and preferably from about 90° to 100° C. By so doing, the hydrolysis reaction can be carried out, and it is an advantageous feature that there is no need to add any other catalyst at this point. During the course of the hydrolysis, a dilute acidic solution of hydrogen bromide is formed which acts as catalyst. In addition, where the aqueous SCDBT/SCMBT solution has been formed by contact with the chlorinated hydrocarbon solution obtained in process S1, the excess hydrogen bromide and part of any residual bromine present in S1 will also be transferred to the aqueous phase, thereby catalysing the reaction right from the start. However, it will be understood that the user is not barred from introducing further amounts of either HBr or some alternative catalyst such as a dilute acid or even a mild alkali, both of which have been tried, into the aqueous reaction mixture in step iv, the disadvantage being the unnecessary additional cost and the requirement to separate out the catalyst.

The reaction period for step iv is particularly dependent upon two factors; one factor is the operating temperature and varies inversely therewith. The second factor is the relative proportions of SCDBT and SCMBT, the period increasing as the proportion of SCMBT increases. Thus, taking both factors into account, the period is selected within the range of from 1 to 15 hours. At one extreme, when SCDBT comprises all or substantially all of the mixture of the two substances, the period is usually selected within the range of from about 1 to 6 hours, and substantially complete hydrolysis has been observed after about 2 to 4 hours when the temperature employed has been just below the boiling point of the aqueous phase. However, at the other extreme, when SCMBT comprises all or substantially all of the mixture, a significantly longer reaction period is chosen, one that is often in the range of 8 to 15 hours, and good conversion has been achieved at around 12 hours reaction time at a temperature of just below the boiling point of the aqueous phase at ambient pressure.

It will be recalled that in the reaction step of process S1, a certain amount of bromine and hydrogen bromide was removed as effluent gas from the vessel. This gas can be scrubbed with water to form a dilute bromide solution, which can be fed into this process S2, most conveniently as the aqueous phase employed in step i of S2. This is not only an enviromentally beneficial activity, by minimising the amount of bromine that is available for discharge, but is an elegant way to transform the waste of one process into a feedstock for a downstream process. Scrubbing can normally be carried out continuously and the product recycled continuously or stored for recycle, as the remaining process constraints show to be most prudent.

The resultant mixture at the end of process S2 contains HBr in addition to the aldehyde (SCAB) and alcohol (SCOL). The compounds can be detected and quantified therein by HPLC techniques, so that by periodic sampling and analysis of the mixture, it is possible to determine easily and conveniently as to when a substantial and/or desired proportion of the SCDBT has been converted to SCAG, and the SCMBT to SCOL to use that measurement as a basis for deciding when to terminate the reaction.

The reaction of process S2 is especially well suited to a batch processing technique, but it will be recognised that it can be engineered to be operated continuously using a flow-through technique, the rate of flow of the reaction mixture through the vessel being adjusted so as to provide the desired reaction period.

It will also be recognised that step ii, is equally well suited to standard continuous or batch processing techniques.

The presence of HBr in the aqueous solution produced in process S2, in many instances in an amount of about 4 to 6 moles per mole of SCDBT/SCMBT that has been hydrolysed, has been found to inhibit the recovery of pure SCAB from solution. The difficulty similarly applies to the oxidation of SCAB to SCUBA (2-chloro 4-sulpho-benzoic acid) by an otherwise convenient route using a peroxyacid, which route will subsequently be described herein in more detail. It has been found that the difficulty can be overcome by removal of the HBr from solution, and this forms the basis of a further aspect of the present invention, namely process S3.

In S3, residual HBr in aqueous solution containing additionally a benzyl alcohol, benzaldehyde or benzoic acid compound can be removed by maintaining the solution at an elevated temperature of above 50° C. and below its boiling point whilst introducing progressively into the solution an effective amount of hydrogen peroxide and sparging the solution with an inert gas. This represents a further aspect of the present invention, either as a process step on its own or in conjunction with and following process S2 and hereinbefore described or process S5 which will be described subsequently herein.

Process S3 is particularly suitably carried out at a temperature of from about 60° to 80° C., being a compromise arising from increasing the operating temperature which not only beneficially encourages and speeds up the generation of bromine from bromide using hydrogen peroxide, but also increasingly promotes the decomposition in situ of hydrogen peroxide. It is preferably carried out in a light-excluded chamber so as to minimise a competitive reaction that is unwanted in S3, namely the dissociation of bromine into radicals, a reaction that is light catalysed.

The amount of hydrogen peroxide to employed depends on the extend of HBr-removal required. The stoichiometric amount is 0.5 moles $H_2O_2$ per mole of HBr and it is preferable to use greater than the stoichiometric amount. In practice the amount of hydrogen peroxide is often selected in the range of 1.1 to 1.5 times the stoichiometric amount. The progressive introduction of hydrogen peroxide into the aqueous/organic mixture during reaction S3 means not only that it is introduced safely, but also can be continued until monitoring of the effluent inert gas suggests that all the bromide has been oxidised to bromine which has itself been removed from solution. By appropriately slowing and finally halting the introduction of peroxide as the monitoring of the effluent gas suggests complete bromine removal is being approached, the total amount of peroxide employed can be minimised, a practice of economic benefit.

The sparging can employ any gas that is inert to the components of the aqueous solution, hydrogen peroxide and bromine. These include the inert gases and preferably nitrogen, in view of its widespread availability. The sparging is preferably effected during the entire period of addition of the hydrogen peroxide, so as to continually remove bromine from the system. The gas is then most preferably passed through a condenser to recover the bromine. It will be recognised that the bromine so recovered can be recycled to process S1 for reaction with further SCT, thereby completing the cycle as regards not only the solvent but also the brominating reagent. Accordingly, there is met the desideratum of being able to carry out at least processes S1 and S2 with recycle of what would otherwise be an environmentally unacceptable pollutant. For the avoidance of doubt, the instant invention includes recycle processes in which process S1 is followed by process S2 and either straightaway or after intervention of process S5 is followed by S3, with the resultant bromine being recovered and recycled to S1.

The process S3 is particularly suited to batch processing techniques or fi a more continuous processing is sought, the use of a series of treatment vessels can be contemplated.

A further aspect of the instant invention comprises the oxidation of SCAB with a peracid, and specifically a percarboxylic acid in process S4. It will be understood that in the presence of bromine/hydrogen bromide, there is an interaction between the two chemicals that results in the destruction of the percarboxylic acid and the failure of the system to oxidise SCAB to SCUBA. It is postulated that the mechanism includes the formation in situ of an oxybromine species by reaction between bromine and the percarboxylic acid and that the species decomposes with release of oxygen. Whilst such a postulation is offered by way of explanation of observation, the invention is not predicted upon its veracity. Thus, according to this further aspect of the instant invention there is provided a process for oxidising SCAB to SCUBA which comprises contacting an aqueous solution of SCAB which is effectively free from inorganic bromine species with at least a stoichiometric amount of a percarboxylic acid and maintaining the mixture at an elevated temperature up to the boiling point of the solution, until at least some SCUBA has formed.

In practice, it is preferable to choose water-soluble peroxyacids and in particular low molecular weight e.g. C1 to C4 percarboxylic acids and especially peracetic acid. In a further feature, it is preferable to generate the peracid in situ by reaction between the corresponding carboxylic acid and hydrogen peroxide. As an alternative, though it is unnecessary and more expensive, the corresponding acid anhydride may be used. It is more convenient in this instance to introduce substantially all the hydrogen peroxide at the start of the reaction so as to optimise the formation of peracid. In such in situ generation, the ratio of hydrogen peroxide to carboxylic acid is usually above 1:1, and preferably from 1.05:1 to about 1.2:1. Use of higher amounts of hydrogen peroxide is possible but wasteful. The peracid is preferably introduced or generated in an amount of at least 1.5 up to about 3 moles per mole of SCAB. The overall reaction period depends at least in part on the temperature which is preferably at least 75° C., and often from 80° to 90° C. and is often selected in the range of 4 to 8 hours.

At the end of the reaction period of process S4, the product SCUBA can be isolated from the aqueous mixture by solvent removal. Further purification and conversion to a solid isolate can be effected by first solvent washing, particularly with an aromatic hydrocarbon such as toluene and then by further solvent removal.

The reaction of process S4 is especially well suited to a batch processing technique, but it will be recognised that it can be engineered to be operated continuously using a flow-through technique, the rate of flow of the reaction mixture through the vessel being adjusted so as to provide the desired reaction period.

It will be recognised that although process S4 is a suitably efficient method for oxidising SCAB to SCUBA, it inevitably introduces an additional component into the reaction mixture, namely a carboxylic acid/percarboxylic acid which remains there at the end of the reaction. It would be extremely elegant and convenient if the oxidation process could be effected without leaving such a residual. Advantageously, the instant inventors have also found a way to achieve that objective and this forms the subject of process S5, a further aspect of the instant invention.

In process S5, there is provided a process for the oxidation of SCAB and SCOL to SCUBA by progressively introducing into an aqueous solution of SCAB and/or SCOL that contains an effective amount of bromide at least a stoichiometric amount of hydrogen peroxide relative to SCAB and SCOL at an elevated temperature with the result that the hydrogen peroxide generates bromine in situ which in turn oxidises the aldehyde and alcohol to carboxylic acid.

It will be recognised that the effective amount of bromide could be introduced specially, if none or insufficient were present, such as at least 1 mole per mole of SCAB/SCOL, and particularly as HBr, but that most advantageously bromide is already present in the aqueous solution obtained from carrying out process S2 as described hereinbefore, provided that process S3 has not been carried out as well. In such a combination of processes, the amount of HBr in solution is normally about 4 to 6 moles per mole of SCAB/SCOL, an amount that is conveniently adequate for the present purpose. Thus, the objective is not only met to avoid introducing a new impurity residue, but even re-employs existing amounts of an already present component and allows the use of a reagent that leaves as residue solely water and oxygen. Consequently, it is an especially preferred combination of processes in the instant invention in which process S5 follows process S2 without intervention of process S3.

The reaction is preferably carried out at a temperature in excess of 50° C. and conveniently at about 60° to 80° C. It will also be noted that in this process S5, the bromine oxidation does not need irradiation to generate radicals, so that it can be carried out in normal enclosed vessels that exclude light.

The stoichiometric amount of hydrogen peroxide is one mole per mole of SCAB, and 2 moles per mole of SCOL. It is particularly preferable to employ at least about 1.5 to 2.5 times the stoichiometric amount of hydrogen peroxide. Complete oxidation has been achieved with about 2x stoichiometry for SCAB and SCOL. The hydrogen peroxide is added gradually during all or part of the reaction period, the length of which in practice often depends upon how much hydrogen peroxide is to be added, and that naturally depends upon the proportions of the alcohol and aldehyde. In practice, the reaction is allowed to continue after addition of the chosen amount of hydrogen peroxide shows that a substantial proportion of the SCAB/SCOL have been converted to SCUBA, so that the total reaction period for S5 is normally not more than about 10 hours. Thus for a starting material that essentially comprises SCAB, the amount of hydrogen peroxide introduced is often from 1.5 to 2.5 moles per mole of SCAB, so that the reaction period is often from 1 to 4 hours. Also, when the starting material essentially comprises SCOL, the amount of hydrogen peroxide introduced is often from 3 to 5 moles per mole of SCOL, so that the reaction period is often from 2 to 8 hours. In many instances, there will be a significant proportion of both starting materials and naurally the amount of hydrogen peroxide and resultant reaction period may be selected pro rata, i.e. at a suitable point between the extremes.

It is important to avoid adding insufficient peroxide to achieve the desired extent of oxidation, but there is naturally an inherent degree of flexibility if process S5 is followed by a bromine-removing process, S3, which also employs hydrogen peroxide to generate bromine. To some extent, a surfeit or deficiency in the addition of the peroxide in one of the two processes can be compensated by an appropriate reduction or extra amount in the other process. For example, if any extra peroxide is added in S5 it merely generates, in the main, bromine and the corresponding amount of peroxide does not therefore need to be added in process S3. This combination is also part of the instant invention. It will be recognised that process S5 and S3 can be carried out very effectively using the same apparatus, the main difference being whether or not an inert gas is actually being sparged through the mixture. It will also be recognised that there is likewise a degree of flexibility in the overall reaction period of S5 when it is followed by the bromine-removing step S3, in that a proportion, preferably minor, of the oxidation reaction can take place during the bromine-removing phase.

The SCUBA can be recovered by solvent removal from the mother liquor which by now consists almost entirely of water, resulting in precipitation of a solid therefrom. The liquor residue by virtue of that fact can itself be recycled to either the preceding process S2 or to an earlier step in process S5.

There is one particular and advantageous benefit of the instant invention. The inventors have found that benzyl alcohol (SCOL) is formed in process S2 by hydrolysis of residual SCMBT and is itself oxidised to SCUBA under broadly similar reaction conditions to those suitable for the formation and further oxidation of SCAB. The full mechanism is not yet known to the instant inventors. It does mean though that one of the possible impurity losses for a process starting with SCT and ending with SCUBA, i.e. losses via intermediate formation of SCMBT is in effect broadly eliminated. Moreover, the fact that both mono and di brominated products can be reacted through to the same final product means that there is an inherent flexibility in the combined process, removing to some extent the need that would be expected to exist in the light of prior experience with nitro-substituted toluene to control conditions in individual stages of the overall process so as to maximise formation of either the one, e.g. SCDBT at the expense of the other, SCMBT.

It will also be observed that the oxidation to SCUBA in process S5 is highly selective. Although it is carried out under conditions that would promote ring bromination, namely the presence of a substantial concentration of bromide in direct contact with the substrate and a high operating temperature, it has been found that such side-reactions occur to no more than an insignificant extent.

The reaction of process S5 is especially well suited to a batch processing technique, but it will be recognised that it can be engineered to be operated continuously using a flow-through technique, the rate of flow of the reaction mixture through the vessel being adjusted so as to provide the desired reaction period.

For the avoidance of doubt, it will be seen that the invention in a final aspect provides an integrated combination of processes, in which in a first stage, SCT is side chain brominated in accordance with process S1, the resultant chloroform solution is contacted with an an aqueous phase and hydrolysed in accordance with process S2, the aqueous phase optionally being formed by stripping exhaust gas from the reaction vessel of process S1, with the separated chlorinated hydrocarbon phase being recycled back to process S1 to start the process again and with the aqueous solution obtained at the end of process S2 being first subjected to process S5 and then to process S3, with the resultant aqueous liquor containing the product SCUBA comprising a marketable product or optionally being recycled to process S2 or S5 after solid product recovery and the separated bromine also being recycled to process S1. Such a combination of stages effectively provides an integrated cycle that employs hydrogen peroxide as the main consumable and bromine as the sole reactive carrier that is essentially recycled.

It will also be seen that the entire process sequence of S1, S2, S5 and S3, in that order can conveniently be carried out in the same vessel, provided that it is suitably equipped, thereby minimising handling of the intermediate stages or in a series of linked vessels, the liquid being pumped or allowed to flow from one vessel to the next at the end of each stage.

Having described the various aspects of the present invention in general terms hereinbefore, embodiments thereof are now described in greater detail by way of example only and which do not in themselves limit the invention.

In the Examples, the apparatus used was chosen in accordance with the preparation scale and comprised a multi-necked 100 ml, 500 ml or 1 liter glass flask that was equipped with a stirrer, a thermometer, reflux condenser and inlet ports for the introduction of the various reagents and a nitrogen sparging inlet line. It was positioned on a water bath to effect heating/temperature control. Either 1 or 2 500 watt tungsten halogen open face floodlamps each having a nominal luminous flux of 9500 lumens were positioned at a distance of approximately 10 cms from the flask wall for use in any Example in which the flask was irradiated.

In the Examples, the terms % conversion (% conv) are employed to indicate the proportion of starting material for that particular reaction which has been consumed during the reaction, and % yield indicates the molar proportion of that selected product based upon the starting material. Unless otherwise stated, the measurements are obtained on materials in solution in the reaction mixture by conventional HPLC techniques using an 'APEX' (trade mark) phenyl reverse phase column. The total % yields shown in the Tables do not reach 100% for two reasons. First, the measurement technique is accurate to about 2 parts in 100, which can produce more apparent discrepancies at high readings, and secondly because there is usually one or more other impurities present in low but detectable amounts.

The abbreviations employed in the Examples for the reagents and products are the same as have been referred to in the text hereinbefore.

EXAMPLES 1 TO 3

Process S1

In these Examples, the flask was charged with a solution of 2-chlorotoluene sulphonic acid (SCT), 56 g (0.25 mole), in chloroform, 500 mls and heated to about 65° C., the refluxing temperature of the mixture. Bromine, 120 g (0.75 moles) was introduced in a very large number of small aliquots during the first 4 hours of the reaction period. The reaction mixture was thoroughly stirred and irradiated throughout the reaction periods given in Table 1. Small samples of the mixture were taken periodically and analysed by HPLC in order to follow qualitatively the progress of the reaction. The reaction was terminated by switching off the illumination and by comparing the HPLC results with standards, a quantitative assessment of the products was made.

TABLE 1

| Ex No | No Lamps | Total reaction period (hrs) | % Conv SCT | % yield SCMBT | % yield SCDBT |
|---|---|---|---|---|---|
| 1 | 1 | 8.5 | 100 | 10 | 85 |
| 2 | 2 | 5 | 100 | 5 | 94 |
| 3 | 2 | 6.5 | 100 | 2 | 94 |

From Table 1, it can be seen that the reaction at all times resulted in quantitative conversion of SCT and that the effect of increasing the total extent of illuminance was to progressively, though not dramatically increase the selectivity of the reaction to producing SCDBT. Both Example 2 and 3 produced products having excellent selectivity.

Repeat trials using similar conditions to those of the Examples 1 to 3 confirmed that the results described in Table 2 are representative.

Repeat trials under otherwise similar conditions in which an equal or greater volume of water compared with chloroform was employed resulted not only in a very poor conversion of SCT, but also the poor selectivity of conversion to SCDBT. These trials confirmed the need to avoid an aqueous phase for process S1 to proceed effectively.

EXAMPLES 4 TO 6

Process S2

In Examples 4 and 5, the starting material was solid SCDBT product obtained in repeat trials of the previous Examples, recovered by precipitation and repurified so that it was substantially free from SCMBT. In these Examples, the solid (3.64 g, $9.5 \times 10^{-3}$M) was taken into solution in water (25 ml) into which was introduced sodium carbonate, 2.64 g in Ex4 and HBr (2 g of 50% w/w aqueous solution) in Ex5. The resultant solution was then heated to boiling point for respectively 2 hours in Ex4 and 1.25 hours in Ex5. In both Examples, HPLC analysis showed 100% conversion of SCDBT and a yield of SCAB in the region of 90%. When recovery of solid product therefrom was attempted by solvent removal, the resultant precipitate was significantly contaminated with bromide which could not be simply washed out.

In Example 6, the starting material was taken into aqueous solution by contacting a chloroform solution obtained by a repeat process according substantially to Example 3 and at the ratio of 150 mls water per 500 mls chloroform, and separated by running off the organic phase in a separation funnel. The resultant aqueous solution was heated to about 100° C. for 2.5 hours and analysis showed that all the SCDBT that was taken into solution had been converted and that greater than 90% (by mole) was in the form of SCAB.

EXAMPLES 7 AND 8

Processes S3 and S4

In these Examples, the starting material comprised SCAB which had been obtained by repeat trials of processes similar to Example 5, to provide an aqueous hydrogen bromide-containing solution. Hydrogen peroxide, as a nominal 70% w/w aqueous solution, 1.1 moles per mole of hydrogen bromide, was introduced into the aqueous solution over a period of about 1 hour whilst maintaining its temperature at about 65° C. and sparging it with nitrogen. When the effluent gas was judged by eye to be free from bromine, sparging was ceased and solid SCAB that is essentially free from HBr and $Br_2$ was obtained by solvent removal.

In each Example, the aldehyde, SCAB, was dissolved in water, into which was introduced glacial acetic acid and hydrogen peroxide at a mole ratio to the acetic acid of 1.1:1 (i.e. slightly excess hydrogen peroxide). The solution was then heated to and maintained at 90° C. for the reaction period until analysis by HPLC indicated that the reaction appeared to be substantially complete. The resultant solutions were then evaporated under vacuum at 50° C. and when the solution became viscous, toluene, about 100 mls was added. Solid product precipitated out. Details of the process and product are summarised in Table 2.

TABLE 2

| Ex No | SCAB moles | Water mls | AcOH moles | Reaction Period (hours) | SCAB % Conv | SCUBA purity % |
|---|---|---|---|---|---|---|
| 7 | 0.25 | 70 | 0.25 | 7 | 100 | 91 |
| 8 | 0.5 | 130 | 0.5 | 5.5 | 100 | 94 |

From Table 2, it can be seen that the reaction proceded very effectively with quantitative conversion of the SCAB and product of a SCUBA solid of high purity.

EXAMPLE 9

Processes S2, S5 and S3

In this Example, a brominated SCT product comprising mainly SCDBT was reacted via SCAB to SCUBA and residual bromide oxidised to bromine and sparged from the solution.

In the first part of the process, i.e. S2, a solid obtained as for Examples 4 and 5, (20 g, 0.05 moles) comprising 85% w/w SCDBT and 15% w/w SCMBT was dissolved in water (30 mls) without any other material being introduced and heated to 100° C. for 4 hours. Analysis using HPLC indicated that all the SCDBT had been quantitatively converted and at least part of the SCMBT had been hydrolysed to SCOL.

Without purifying or otherwise treating the solution obtained at the end of the S2 process, so that it contained about 0.1 moles of HBr in addition to SCAB and some SCOL, the aqueous mixture was cooled to 60° C. and aqueous hydrogen peroxide solution (nominal 70% w/w, 0.2 moles, 7.2 g approx. of solution) was introduced very slowly over a period of 2 hours. The total reaction period at 60° C. was 5.5 hours. During the course of this period analysis showed that SCUBA was being formed. This demonstrates an S5 process.

Again without separating or purifying the resultant solution, nitrogen gas was sparged into the solution which continued to be maintained at 60° C., whilst a further amount of hydrogen peroxide (0.1 mole, 3.6 g approx of a nominal 70% w/w solution) was introduced during the subsequent hour. Sparging continued until the effluent gas was visually free from bromine. This is a further example of process S3.

At the end of the processes, analysis by HPLC confirmed that 100% of SCDBT had been converted and that the yield of SCUBA (12.4 g) was about 110% of the theoretical yield from solely SCDBT and 93% based on the mixed SCDBT/SCMBT starting material. This Example demonstrates and confirms that the hydroylysis and oxidation processes operate upon both the mono and di-brominated compounds to yield SCUBA rather than operating upon only one of them. In particular, the Example shows that SCMBT is hydrolysed and oxidation of the hydrolysed compounds with bromine does not halt at the aldehyde stage or produce bromine-substituted derivatives. Beyond that, it shows not only that each of the two separate stages provided yields in excess of 95% but also that it was perfectly possible to combine all three processes into a multi-step process which recovered the bromine oxidant and thus showed, when Example 6 is included the viability and elegant simplicity of the closed loop process combining S1, S2, S5 and S3 in that order.

EXAMPLE 10

In this Example, SCT was subjected in successive stages to bromination, hydrolysis and oxidation to SCUBA.

Bromine was added gradually in two fractions (32 g and 16 g=48 g, 0.3 moles) into a solution of SCT (22.5 g, 0.1 mole) in chloroform (250 mls) over two period totalling 3.5 hours whilst irradiating the mixture with 2 floodlamps, and maintaining a reaction temperature of about 65° C. Reaction was permitted to continue for a further 5 hours, part of which separated the periods of bromine addition, under the same conditions and also during an additional 1.5 hours with irradiation by a single floodlamp, and a reaction temperature of about 55° C. Analysis of the reaction mixture indicated that quantitative conversion of SCT has been achieved, some bromine remained and that approximately 60% of the product comprised SCMBT and 40% SCDBT.

The resultant solution was contacted with 30 mls of demineralised water (DMW) to extract SCMBT and SCDBT and HBr, separated and the aqueous phase retained. The organic phase was likewise contacted with a further 10 mls DMW, and the two aqueous phases were combined and heated to 95°-100° C. for about 10 hours. Analysis showed that a small residue of SCMBT remained, but the remaining SCMBT and SCDBT had been hydrolysed. A further 10 mls water was added and the mixture refluxed for a further 4 hours.

The resultant aqueous solution was brought to a temperature of 80° C. and hydrogen peroxide (7.5 g of a 70% w/w solution) was introduced gradually over a period of 5 hours. Nitrogen gas was then blown through the solution during the gradual addition of a further amount of 2.5 g 70% w/w hydrogen peroxide. The sparging was discontinued when analysis indicated that no further bromine was being removed and the solution contained less than 0.25% hydrogen peroxide.

The aqueous solution was then dewatered using a rotary evaporator and any residual water was removed by azeotroping with toluene. The resultant solid was dried in a vaccuum dessicator and analysed by HPLC. The solid contained 23.24 g SCUBA, which represents a yield based upon SCT starting material of 91.1%.

EXAMPLES 11 TO 16

These Examples were conducted by dissolving SCT (0.1 mole, 22.4 g) in either chloroform, referred to as cfm in the Table below or 1,1,2-trichloroethane, referred to as tce and introducing a selected amount of bromine gradually over a period of 4 hours, the mole ratio of bromine to SCT being lower than in Example 1 so as to encourage the formation of SCMBT rather than SCDBT. The reaction heated to the specified reaction temperature and illuminated as in Example 1 during the bromine introduction and for a further 2 hours. The resultant solution was analysed by glc for residual SCT, and both SCMBT and SCDBT. The process variations and results are summarised in Table 3 below.

TABLE 3

| Ex No | Solvent amount mls | Amount of Br₂ moles | Temp °C. | Analysis of final solution to nearest integer, % w/w | | |
|---|---|---|---|---|---|---|
| | | | | SCT | SCMBT | SCDBT |
| 11 | cfm 200 | 0.25 | 65 | 2 | 69 | 29 |
| 12 | cfm 200 | 0.2 | 65 | 4 | 75 | 22 |
| 13 | cfm 200 | 0.18 | 65 | 7 | 75 | 18 |
| 14 | tce 200 | 0.18 | 80 | 2 | 70 | 28 |
| 15 | tce 150 | 0.18 | 80 | 1 | 68 | 30 |
| 16 | tce 100 | 0.18 | 80 | 5 | 77 | 18 |

From Table 3, it can be seen that the proportion of SCMBT in the final solution was substantially greater than that obtaining in the product of Example 1. When the mole ratio of bromine to substrate was reduced to 1.8:1, as in Examples 12 to 15, it will be seen that nearly complete conversion of the SCT was still possible, and was encouraged by the slightly higher reaction temperature that could be employed with trichloroethane.

EXAMPLE 17

In this Example, a variation of Example 10 was employed in which the initial solution comprised approximately 0.156 moles of SCT plus 0.012 moles of 4-sulphotoluene and about 0.031 moles of other chlorosulphotoluene compounds dissolved in 1,1,2-trichloroethane (300 mls).

In the bromination stage, the bromine was introduced in two portions, the first (0.25 mole) during 4 hours and the second (0.1) mole over 2 hours, each portion being followed by an additional reaction period of 5 hours. The solution was irradiated with a single floodlamp and maintained with cooling to the range 79° to 85° C.

In the hydrolysis stage, the reaction products of the bromination stage were extracted with 50 mls DMW and then with 25 mls DMW, which were combined to provide 75 mls aqueous solution that was heated to 95°-100° C. for 12 hours.

The subsequent stages comprising oxidation of the alcohol/aldehyde to SCUBA, the removal of bromine and recovery of the solid product were conducted the same as in Example 10.

The resultant solid weighed 40.4 g, having a SCUBA content of 86% w/w, i.e. 0.147 moles. This demonstrates that even when the major product of the bromination stage is SCMBT, an excellent conversion of SCT to SCUBA can be achieved.

We claim:

1. A multi-stage process for the preparation of 4-sulpho-2-chlorobenzoic acid (SCUBA) from 2-chloro-4-toluene sulphonic acid (SCT) characterised in that in stage a, the methyl substituent in SCT is selectively brominated to the mono and/or dibrominated compound by reacting the SCT in a substantially anhydrous solvent with bromine that has been dissociated into radicals by radiation, in stage b, the selectively brominated compounds produced in stage a are extracted into an aqueous phase and hydrolysed to the corresponding alcohol or aldehyde in the presence of hydrogen bromide and in stage c, the aqueous solution of aldehyde/alcohol produced in stage b is oxidised to SCUBA by reaction with a percarboxylic acid in the substantial absence of hydrogen bromide or by reaction with bromine.

2. A multi-stage process according to claim 1 characterised in that in stage a, the anhydrous or substantially anhydrous solvent for SCT is selected from chloroform and trichloroethane, the SCT is contacted with at least 1.6 moles of bromine per mole of SCT at a temperature of from 30° C. to the boiling point of the reaction mixture and the reaction mixture is irradiated with bromine-dissociating radiation until at least some 1-dibromomethyl-2-chloro-4-sulphobenzene (SCDBT) has formed.

3. A process for the side chain bromination of an alkyl substituent of a further substituted benzene compound which can be incorporated as stage a in a multi-stage process for the preparation of SCUBA from SCT described in claim 1 and which bromination process is characterised in that the alkylbenzene compound employed is 2-chloro-4-toluene sulphonic acid (SCT), which is dissolved in an anhydrous or substantially anhydrous solvent selected from chloroform and trichloroethane and is contacted with at least 1.6 moles of bromine per mole of SCT at a temperature of from 30° C. to the boiling point of the reaction mixture and the reaction mixture is irradiated with bromine-dissociating radiation until at least some 1-dibromomethyl-2-chloro-4-sulphobenzene (SCDBT) has formed.

4. A process according to claim 2 or 3 characterised in that the concentration of SCT is selected in the range of 0.25 to 1.25M.

5. A process according to claim 2 or 3 characterised in that from 1.8 to 2.2 moles of bromine per mole of SCT is consumed, whereby the major reaction product is 1-bromomethyl-2-chloro-4-sulphobenzene (SCMBT).

6. A process according to claim 5 characterised in that the the solvent comprises 1,1,2-trichloroethane and the reaction temperature is selected in the range of 70° to 85° C.

7. A process according to claim 2 or 3 characterised in that from 2.8 to 4.0 moles of bromine per mole of SCT is consumed, whereby the major reaction product is 1-dibromomethyl-2-chloro-4-sulphobenzene.

8. A process according to claim 7 characterised in that the solvent comprises chloroform and the reaction temperature is selected in the range of 50° to 70° C.

9. A process according to claim 2 or 3 characterised in that bromine is introduced gradually into the reaction mixture over a period of from 2 to 6 hours.

10. A process according to claim 2 or 3 characterised in that the reaction is permitted to continue until the proportion of SCT remaining unreacted has reached 5% or less of the initial amount.

11. A multi-stage process according to claim 1 characterised in that stage b is carried out by the steps of:
   i. abstracting the brominated derivatives of SCT, namely SCDBT and SCMBT into aqueous solution by contacting the SCDBT and SCMBT in a non-aqueous phase with water,
   ii. separating the aqueous solution of SCDBT and SCMBT from any residual non-aqueous phase that has a boiling point significantly below 85° C.,
   iii. bringing the aqueous solution to a temperature of at least about 85° C. up to the boiling point of the solution, and
   iv. maintaining the aqueous solution at that temperature until at least a proportion of the SCDBT and the SCMBT has been hydrolysed to SCAB and to SCOL respectively.

12. An hydrolysis process for the preparation of 2-chloro-4-sulpho-benzaldehyde (SCAB) from SCDBT and 2-chloro-4-sulphobenzyl alcohol (SCOL) from SCMBT, which process can be incorporated as stage b in a multi-stage process for the preparation of SCUBA from SCT described in claim 1 and which hydrolysis process is characterised by the steps of:
   i. abstracting SCDBT and SCMBT into aqueous solution by contacting the SCDBT and SCMBT in a non-aqueous phase with water,
   ii. separating the aqueous solution of SCDBT and SCMBT from any residual non-aqueous phase that has a boiling point significantly below 85° C.,
   iii. bringing the aqueous solution to a temperature of at least about 85° C. up to the boiling point of the solution, and
   iv. maintaining the aqueous solution at that temperature until at least a proportion of the SCDBT and the SCMBT has been hydrolysed to SCAB and to SCOL respectively.

13. A process according to claim 11 or 12 characterised in that the non-aqueous phase for the SCMBT and/or SCDBT in step i. comprises a solution in chloroform or 1,1,2-trichloroethane.

14. A process according to claim 11 or 12 characterised in that from 0.2 to 1.0 moles of water is employed in step i. per mole of SCMBT/SCDBT.

15. A process according to claim 11 or 12 characterised in that step iv is continued for a reaction period selected in the range of from 1 to 15 hours, and taking into account the relative proportions of SCMBT and SCDBT, the higher the proportion of SCMBT, the longer the period.

16. A process according to claim 11 or 12 characterised in that the water employed in step i comprises an aqueous solution of hydrogen bromide.

17. A process according to claim 16 characterised in that the aqueous solution of hydrogen bromide is obtained by passing the off-gasses from stage a through water.

18. A multi-stage process according to claim 1 characterised in that stage c is carried out by contacting an aqueous solution of SCAB which is effectively free from inorganic bromine species with at least a stoichiometric amount of a percarboxylic acid and maintaining the mixture at an elevated temperature up to the boiling point of the solution, until at least some SCUBA has formed.

19. A process for oxidising SCAB to 4-sulpho-2-chlorobenzoic acid (SCUBA) which can be incorporated as stage c in a multi-stage process for the preparation of SCUBA from SCT described in claim 1 and which oxidation process is characterised by contacting an aqueous solution of SCAB which is effectively free from inorganic bromine species with at least a stoichiometric amount of a percarboxylic acid and maintaining the mixture at an elevated temperature up to the boiling point of the solution, until at least some SCUBA has formed.

20. A process according to claim 18 or 19 characterised in that the percarboxylic acid is selected from C1 to C4 aliphatic percarboxylic acids.

21. A process according to claim 18 or 19 characterised in that the peracid is employed in a mole ratio of from 1.5 to 3 moles per mole of SCAB.

22. A process according to claim 18 or 19 characterised in that the reaction is conducted at a temperature of from about 80° to about 90° C. for a period of from 4 to 8 hours.

23. A multi-stage process according to claim 1 characterised in that stage c is carried out by progressively introducing into an aqueous solution of SCAB and/or SCOL that contains an effective amount of bromide at least a stoichiometric amount of hydrogen peroxide relative to SCAB and SCOL at an elevated temperature with the result that the hydrogen peroxide generates bromine in situ which in turn oxidises the aldehyde and alcohol to carboxylic acid.

24. A process for the oxidation of SCAB and SCOL to SCUBA which can be incorporated as stage c in a multi-stage process for the preparation of SCUBA from SCT described in claim 1 and which oxidation process is characterised by progressively introducing into an aqueous solution of SCAB and/or SCOL that contains an effective amount of bromide at least a stoichiometric amount of hydrogen peroxide relative to SCAB and SCOL at an elevated temperature with the result that the hydrogen peroxide generates bromine in situ which in turn oxidises the aldehyde and alcohol to carboxylic acid.

25. A process according to claim 23 or 24 characterised in that the reaction is conducted at a temperature of from about 60° to 80° C.

26. A process according to any one of claim 24 or 25 characterised in that the amount of hydrogen peroxide introduced is from 1.5 to 2.5 times the stoichiometric amount.

27. A process according to claim 24 or 25 characterised in that the hydrogen peroxide is introduced over a reaction period selected in the range of from 1 to 8 hours taking into account the proportion of SCOL in the combined amount of SCOL and SCAB, the higher the proportion of SCOL, the longer the reaction period.

28. A multi-stage process according to claim 1 characterised in that the organic solvent that is separated from the aqueous phase in stage b is dewatered, contacted with a further amount of SCT and recycled to stage a.

29. A multi-stage process according to claim 1 characterised in that bromine is removed from solution, either prior to stage c if a percarboxylic acid is employed therein or after stage c is completed if bromine is employed therein, by introducing aqueous hydrogen peroxide in at least a stoichiometric amount progressively into the aqueous solution containing the hydrogen bromide thereby oxidising the bromide to bromine, sparging the solution with an inert gas, which carries the bromine out of solution, the bromine is recovered from the gas and recycled to stage a.

30. A process according to claim 29 characterised in that from 1.1 to 1.5 times the stoichiometric amount of hydrogen peroxide is employed.

31. A process according to either of claims 29 or 30 characterised in that the bromide oxidation is effected at a temperature of from 60° to 80° C.

* * * * *